US012648824B2

(12) United States Patent
Winters

(10) Patent No.: US 12,648,824 B2
(45) Date of Patent: *Jun. 9, 2026

(54) CATHETER ORGANIZER FOR SURGICAL PROCEDURES

(71) Applicant: Atlantic Health System, Inc.,
Morristown, NJ (US)

(72) Inventor: Stephen Leslie Winters, Morris Plains,
NJ (US)

(73) Assignee: Atlantic Health System, Inc.,
Morristown, NJ (US)

( * ) Notice: Subject to any disclaimer, the term of this
patent is extended or adjusted under 35
U.S.C. 154(b) by 70 days.

This patent is subject to a terminal dis-
claimer.

(21) Appl. No.: 18/907,007

(22) Filed: Oct. 4, 2024

(65) Prior Publication Data

US 2025/0025254 A1     Jan. 23, 2025

Related U.S. Application Data

(63) Continuation of application No. 18/510,202, filed on
Nov. 15, 2023, now Pat. No. 12,257,019, which is a
continuation of application No. 16/926,227, filed on
Jul. 10, 2020, now Pat. No. 11,850,018.

(60) Provisional application No. 62/872,525, filed on Jul.
10, 2019.

(51) Int. Cl.
*A61B 46/23*         (2016.01)
*A61M 25/02*         (2006.01)

(52) U.S. Cl.
CPC ............. *A61B 46/23* (2016.02); *A61M 25/02*
(2013.01); *A61B 2046/234* (2016.02); *A61M*
*2025/024* (2013.01)

(58) Field of Classification Search
CPC ... A61B 2046/234; A61B 46/23; A61B 46/10;
A61B 2050/0066; A61M 2025/024;
A61M 2025/0206; A61M 2025/0226;
A61M 2025/02; A61M 2025/0266; A61M
2025/026; A61M 2025/0253; A61M
5/1414; A61M 5/1418; A61M 2209/08;
B65D 63/10; B65B 63/12; F16B 2/10;
F16B 2/06; F16B 2/248; F16B 2/20;
F16B 2/26; F16L 3/08; F16L 3/1075;
(Continued)

(56) References Cited

U.S. PATENT DOCUMENTS 3,696,920 A * 10/1972 Lahay .................... A61B 50/30
206/370
3,881,474 A      5/1975 Krzewinski
4,040,418 A      8/1977 Collins
(Continued)

FOREIGN PATENT DOCUMENTS

EP        0736287 B1    12/1996
EP        2526889 A1    11/2012

*Primary Examiner* — Camtu T Nguyen
(74) *Attorney, Agent, or Firm* — The McHattie Law Firm;
William Smith

(57) ABSTRACT

A catheter organizer for organizing one or more catheters
during a surgical procedure includes a drape and a plurality
of clips tethered to the drape in an arrayed pattern. The clips
are arranged to receive the one or more catheters such that
the catheters move longitudinally and rotate within said each
clip. Each clip has movable members for reversibly chang-
ing the clip from an open configuration to a closed configu-
ration by manipulation of the movable members.

5 Claims, 8 Drawing Sheets

(58) Field of Classification Search
CPC ......... F16L 3/1083; F16L 3/1207; F16L 3/11;
Y10T 24/1498
See application file for complete search history.

(56) References Cited

U.S. PATENT DOCUMENTS

| | | | |
|---|---|---|---|
| 4,134,398 A | | 1/1979 | Scrivens |
| 4,417,710 A | | 11/1983 | Adair |
| 4,605,397 A | * | 8/1986 | Ligon ................. A61M 5/1418 |
| | | | 604/179 |
| 4,664,103 A | | 5/1987 | Martin et al. |
| 4,795,429 A | * | 1/1989 | Feldstein ........... A61M 5/1407 |
| | | | 604/82 |
| 4,988,062 A | * | 1/1991 | London ............... A61G 7/0503 |
| | | | 604/80 |
| 5,624,403 A | * | 4/1997 | Jaquith ................ A61M 25/02 |
| | | | 604/179 |
| 11,850,018 B2 | | 12/2023 | Winters |
| 2006/0169290 A1 | | 8/2006 | Harris et al. |
| 2011/0083983 A1 | * | 4/2011 | Walters ................. A61B 50/20 |
| | | | 206/370 |
| 2012/0298115 A1 | | 11/2012 | Haines et al. |
| 2014/0259557 A1 | | 9/2014 | Egan |
| 2022/0022991 A1 | * | 1/2022 | Ballard ................. A61B 46/23 |
| 2024/0081935 A1 | | 3/2024 | Winters |

* cited by examiner

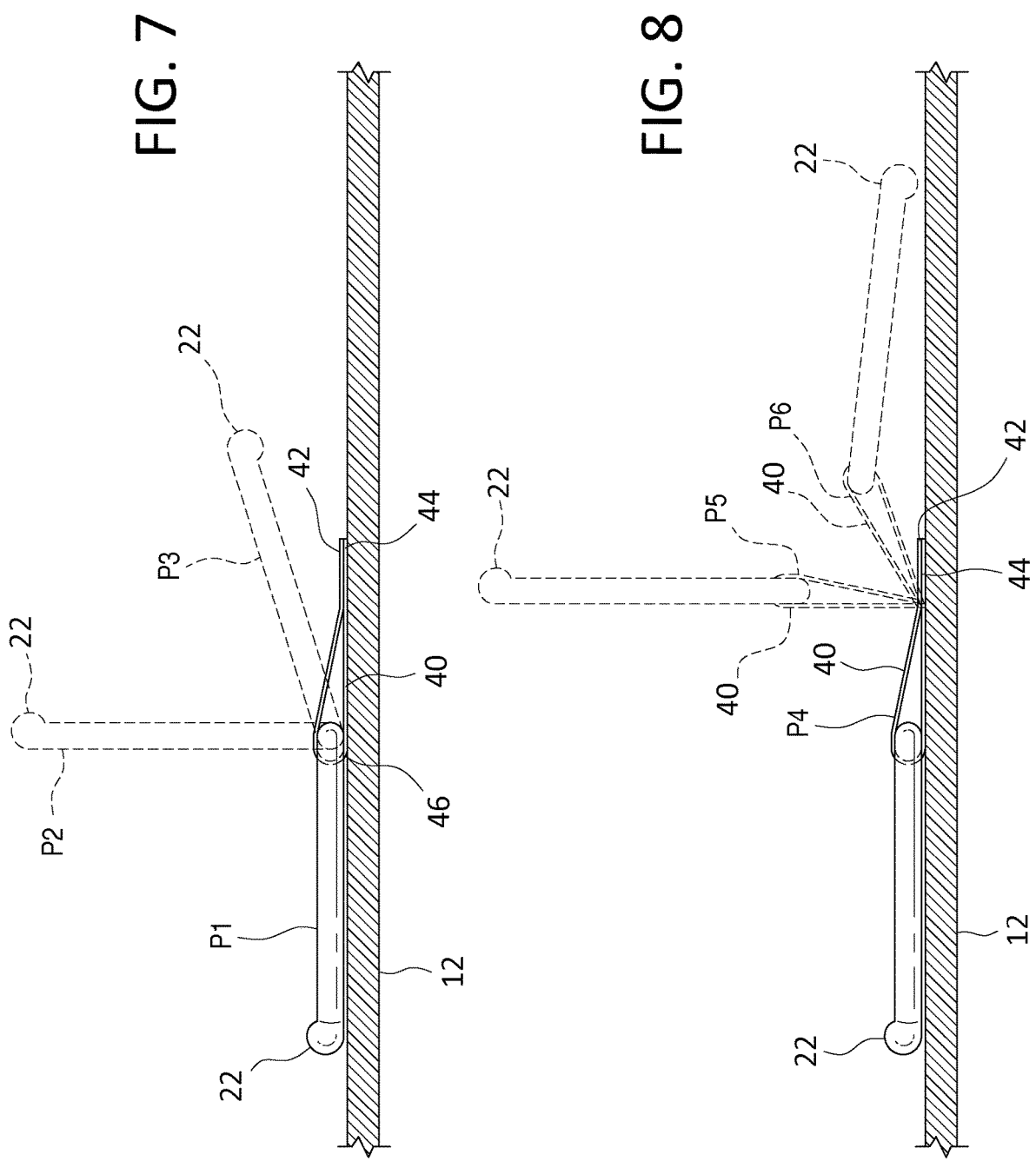

CATHETER ORGANIZER FOR SURGICAL PROCEDURES

The present application is a continuation of U.S. patent application Ser. No. 18/510,202, which was filed on Nov. 15, 2023 and is a continuation of U.S. patent application Ser. No. 16/926,227, which was filed on Jul. 10, 2020 and issued as U.S. Pat. No. 11,850,018 on Dec. 26, 2023, and which claims the benefit of U.S. Provisional Patent Application No. 62/872,525, which was filed on Jul. 10, 2019. The disclosures made in the aforesaid patent applications are incorporated herein by reference.

FEDERALLY SPONSORED RESEARCH AND DEVELOPMENT

No federal funding was used in the research or development of the invention disclosed herein.

TECHNICAL FIELD OF INVENTION

The present invention is related to the field of medical equipment for invasive surgical procedures, and, more particularly, to the field of organizing and managing catheters, cables, tubes, wires and other elongated elements of surgical implements and/or other required devices and implements prior to and during the surgical procedure.

BACKGROUND OF THE INVENTION

During invasive cardiac electrophysiology procedures, typically two or more percutaneous, intravascular catheters are passed into the heart via the femoral veins and arteries. An additional catheter may be passed into the heart via the right internal jugular vein. Over the course of the ensuing procedure, which may last from one to eight hours, these catheters are left in specific positions for various times, or are rotated, advanced, withdrawn, or exchanged. The catheters may be of electrically conductive types (e.g., electrodes), hollow lumen tubes, ultrasound probes, or other devices that employ elongated elements that are structurally and/or operationally similar to cables or tubes. In turn, some of these elements may be contiguous along their lengths, such as when an electrode catheter is used in conjunction with intravenous tubing to enable irrigation or cooling.

Typically, these catheters run the length of the surgical table to interface with various recording, mapping, and ablation systems, ultrasound systems, intravenous solution bags, and other modules. During a given procedure, the catheters and their connecting cables or tubing often become entangled with one another. As a result, the desired position of a given catheter in the heart may be disturbed due to forced movement of other catheters. In addition, intravenous tubing to the catheters and/or sheaths may become twisted or malfunction. Consequently, catheter positions that would enable effective recording of electrical signals and ablation may be lost, myocardial perforations may occur, and blood clot or air-related strokes may develop. In essence, the undesired movement of the catheters can prolong procedures, reduce the effectiveness of procedures, and increase the risk of serious complications, including death.

SUMMARY OF THE INVENTION

In an embodiment, the present invention provides a catheter organizer that includes a surgical drape and an array of catheter retaining means arranged to removably receive one or more catheters and other surgical implements and limit their respective ranges of movement. In an embodiment of the present invention, a catheter organizer includes a surgical drape having an array of collapsible clips for receiving a catheter, each of the clips retained by a tethering means attached to the surgical drape. In an embodiment, the tethering means are strips of fabric. In an embodiment, each strip of fabric is in the form of a loop having two ends attached to the drape, each clip being retained by a respective loop. In an embodiment, the clips and loops are arranged to limit the lateral and vertical movement of a catheter received in the clip relative to the surface of the drape, while allowing the catheter to be advanced or withdrawn longitudinally through the clip and/or rotated within the clip. In an embodiment, each clip has an interlocking mechanism for holding the clip closed. The mechanism may be reversible, allowing the clip to be reopened. In an advantageous embodiment, the catheter retaining means create multiple non-conflicting pathways, facilitating use and access to the catheters and other implements, and reducing conflict and confusion among them.

BRIEF DESCRIPTION OF DRAWINGS

For a better understanding of the present invention, reference is made to the following detailed description of the exemplary embodiments considered in conjunction with the accompanying drawings, in which:

FIG. 7 is a side view of the clip, fabric strip, and drape of FIG. 6, the fabric strip shown in a first position and the clip shown in first, second, and third positions;

FIG. 8 is a side view of the clip, fabric strip, and drape of FIG. 7, the fabric strip shown in first, second, and third positions;

DETAILED DESCRIPTION OF THE INVENTION

Figure 1:
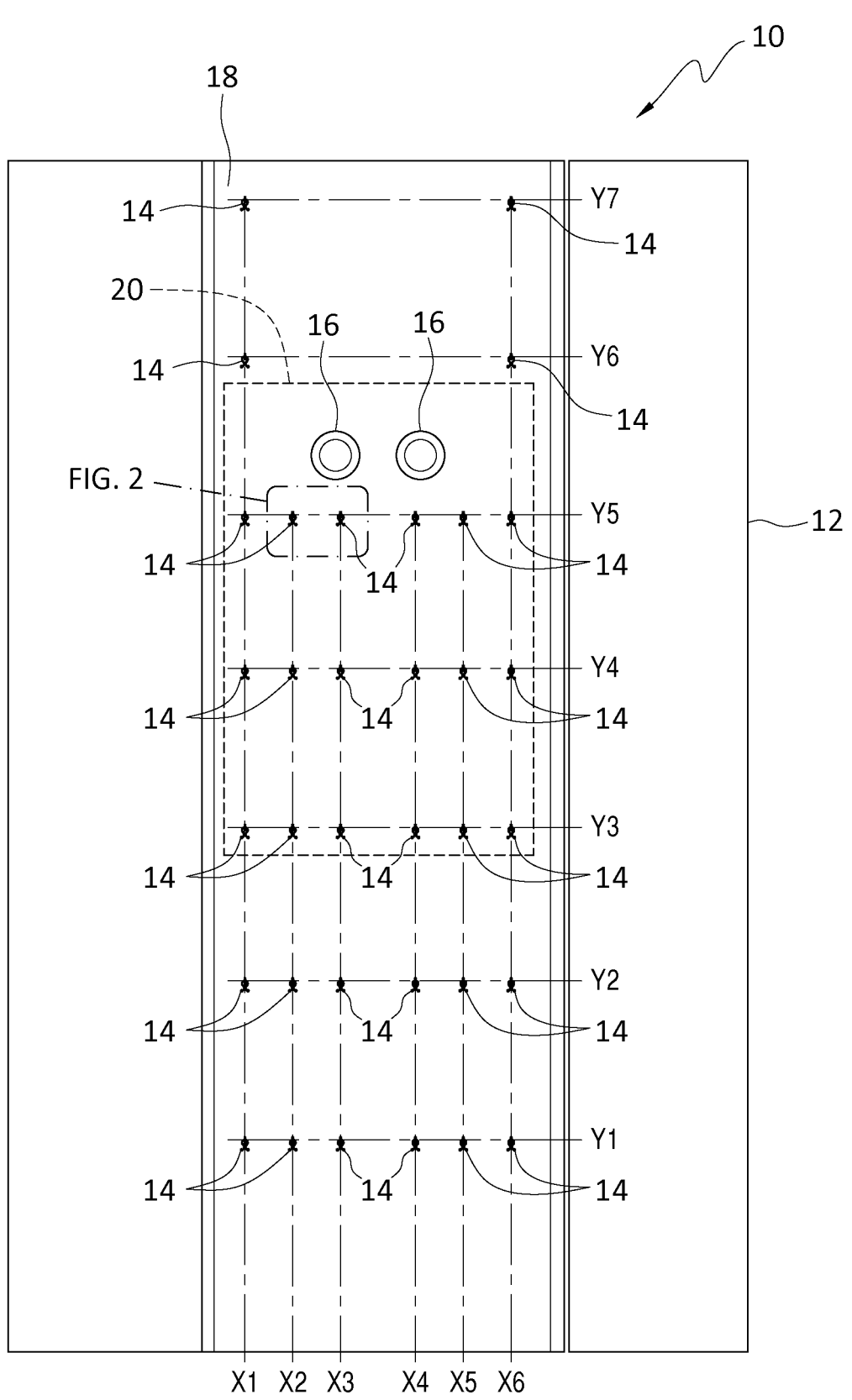
FIG. 1 is a top down schematic plan view of a catheter organizer according to an embodiment of the present invention.

Reference will now be made in detail to one or more embodiments of the invention, examples of which are schematically illustrated in the accompanying drawings. The embodiments are intended to provide an explanation of the invention, and are not meant as a limitation of the invention. For example, features illustrated or described as part of one embodiment may be utilized or combined with features of another embodiment to yield a new embodiment. Further, the features of the embodiment are not limited as to dimensions, number, materials, or other variable features consistent with the use and operation of the invention.

As used herein, "attach" or "attached" refer to the bonding, fusing, joining, adhering, connecting, or the like, of a first element to a second element. Two elements may be considered to be attached when they are bonded, fused, joined, adhered, connected, or the like, directly to each other, with no intervening element, or indirectly to each other, such as when each of a first element and a second element is attached to an intervening element between them.

As used herein, "retain" or "retained" refer to the arrangement of two elements such that one element limits the range of motion of the other element and/or prevents separation of the two elements during normal operation of the invention.

As used herein, "vertical" and "horizontal" directions are taken relative to a surface, such as the broad surface of a drape in a spread arrangement.

As used herein, "longitudinal" and "longitudinally" refer to the longest axis of an elongated object or a direction substantially coinciding with or parallel to a longitudinal axis.

As used herein, "lateral" or "laterally" refer to an axis generally perpendicular to a longitudinal axis or a direction substantially coinciding with or parallel to a lateral axis. Unless otherwise described, "lateral" and "laterally" should be understood to refer to directions generally coinciding with or parallel to an extended surface, such as the surface of a drape in a spread arrangement.

In figures showing a plurality of identical elements, or structurally similar elements performing the same function, the same reference number may be used for all such elements. Where otherwise identical elements are differentiated in the description of the invention, the reference numbers may be distinguished by the addition of a lowercase letter to distinguish the elements. Where the same element is shown in more than one figure, the same reference number may be used on each figure on which the element is shown.

The present disclosure uses the terms "catheter" and "tube" as representatives of the elongated elements of surgical tools and their associated devices. Such elongated elements include, but are not limited to, catheters, tubes, sheaths, wires, optical fibers, and similarly shaped items, any of which may be used with the present invention.

Although the exemplary embodiments discussed herein are primarily directed to the organization and retention of catheters and other elongated elements of surgical tools, it will be understood from the disclosure that catheter retaining means may also be provided that are suitable for organizing other implements that may be secured to the drape for access during surgical procedures.

Figure 2:
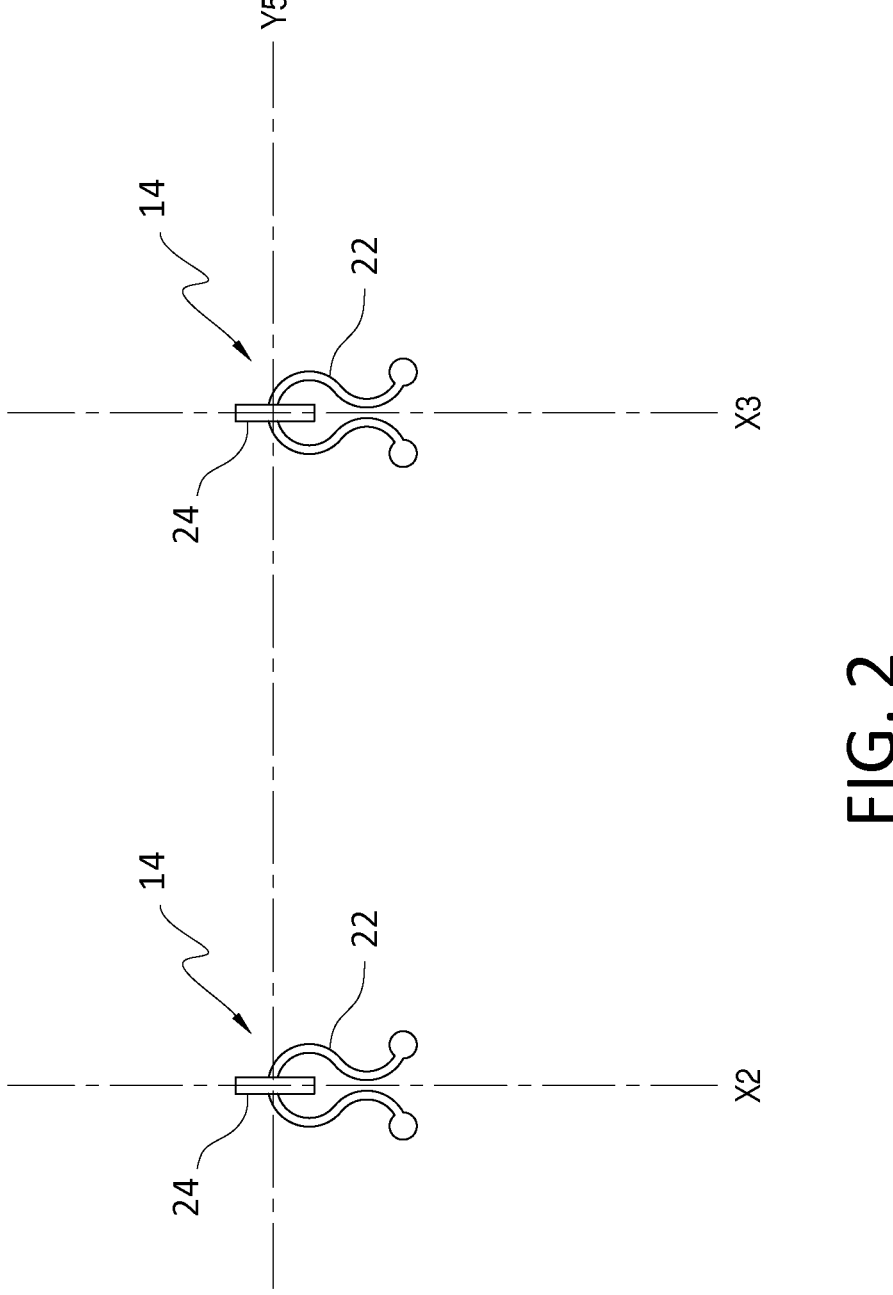
FIG. 2 is an enlarged detail of FIG. 1.

Turning to FIG. 1, taken in combination with FIG. 2, an exemplary embodiment of a catheter organizer 10 of the present invention comprises a drape 12 having a plurality of catheter retaining means 14 attached thereto. The exemplary drape 12 is a full-body drape having fenestrations 16 for providing access to a patient's body from the upper surface 18 of the drape 12. In the exemplary embodiment, the drape 12 also has a pad 20 affixed to or enclosed within the drape 12. The pad 20 may be provided to strengthen or reinforce the drape 12, or for other purposes, such as providing the surgical team with protection from radiation associated with imaging techniques. In other embodiments of the invention, a pad 20 is not provided.

Drapes that are suitable for use in the present invention are formed of sheet materials that can be rendered sterile. In embodiments of the invention, the drapes are not full-body drapes, but may have shapes that are adapted to protect specific parts of the body according to the surgical procedure that is to be performed. Suitable drapes may have sufficient strength to resist being deformed and/or torn when forces are applied to the attached catheter retaining means.

In the exemplary embodiment schematically illustrated in FIGS. 1 and 2, the catheter retaining means 14 are located at the intersections of longitudinal lines X1 through X6 and lateral lines Y1 through Y7. The longitudinal and lateral lines are not physical elements of the catheter organizer 10, but are included in FIGS. 1 and 2 to aid in explaining the exemplary embodiment. It is not necessary for the catheter retaining means 14 to be arranged in the illustrated fashion for an embodiment of a catheter to be included within the scope of the present invention. In embodiments of the present invention, the catheter retaining means 14 are arranged to provide one or more pathways for routing one or more catheters or other elongated elements along or across the drape 12. Other retaining means (not shown) may be provided to retain implements other than catheters or similar elongated elements at locations on the drape 12 where they will be conveniently accessed by the practitioners during surgery. Non-limiting examples of such other retaining means include pockets, and clips and/or loops without clips formed from or attached directly to the drape 12 by sewing, gluing, or loop-and-hook mechanisms (e.g., those used in VELCRO).

FIG. 2 presents an enlarged detail of the catheter organizer 10 which includes the catheter retaining means 14 located at the intersections of longitudinal lines X2 and X3 with lateral line YS. In the exemplary embodiment of FIGS. 1 and 2, the catheter retaining means 14 comprises a clip 22 and tethering means 24. The catheter retaining means 14 is arranged so that the clip 22 is indirectly attached to the drape 12 by the tethering means 24. The tethering means 24 may be attached directly to the drape 12, or may be attached to a reinforcing pad or strip (not shown) which is itself directly or indirectly attached to the drape 12. The clip 22 may be moved relative to the drape 12, but its range of movement is limited by the tethering means 24.

Figures 3, 9:
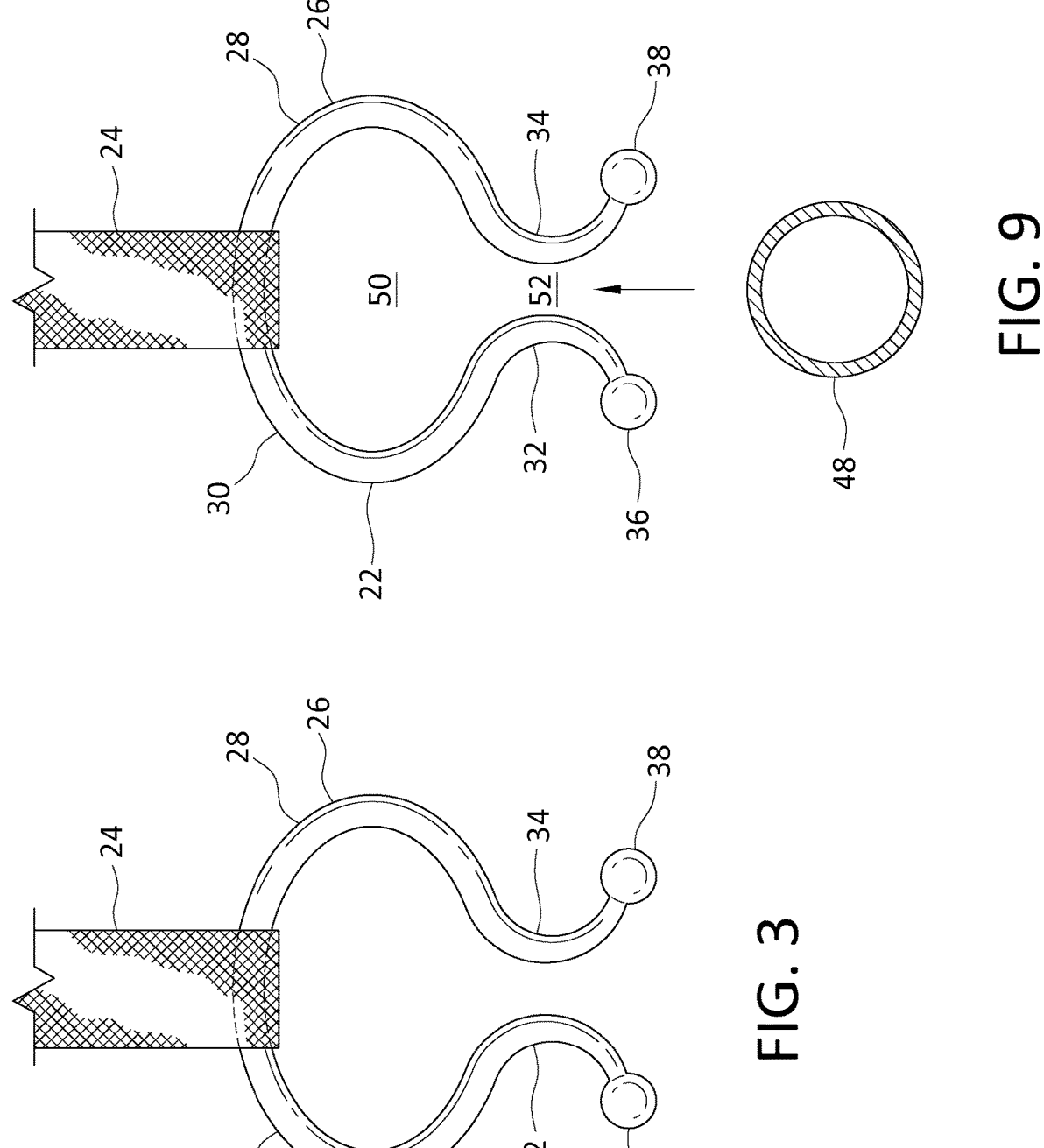
FIG. 3 is a front elevation view of a clip and fabric strip according to an embodiment of the present invention in an open configuration.
FIG. 9 is a front elevation view of the clip and fabric strip of FIG. 3 with the clip receiving a tube according to an embodiment of the present invention, the tube shown in an axial cross-sectional view.
Figure 4:
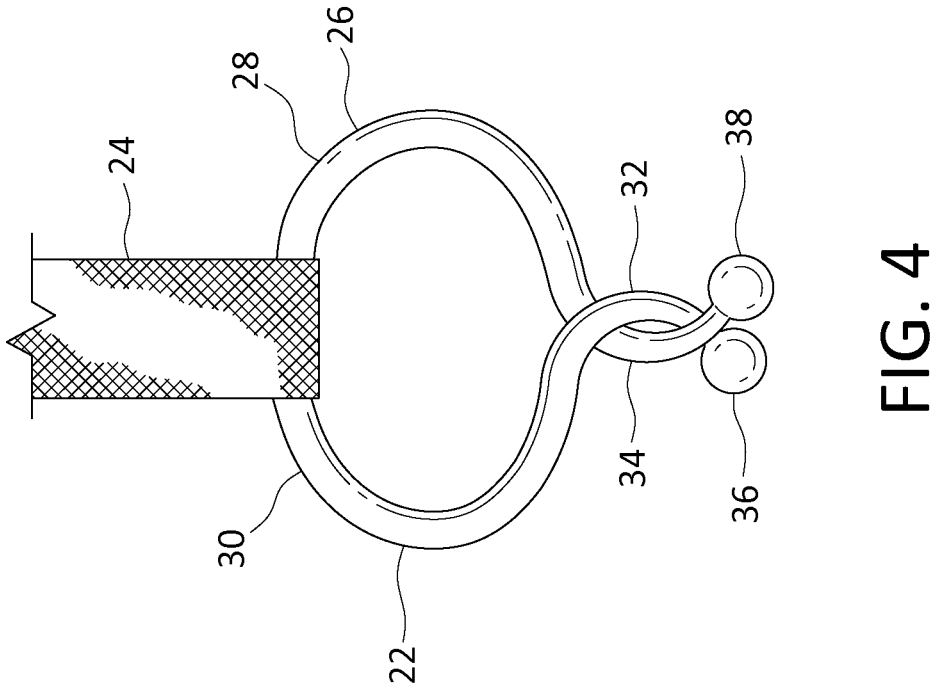
FIG. 4 is a front elevation view of the clip and fabric strip of FIG. 3 in a closed configuration.

Referring to FIGS. 3 and 4, an exemplary clip 22 suitable for use in the present invention is a self-locking clip that can moved from an open configuration (FIG. 3) to a closed and locked configuration (FIG. 4). In the present exemplary embodiment, the clip 22 has the same general configurations as the EZ-TWIST cable tie provided by TACH-IT of Hackensack, NJ. Clips or ties having other configurations may be suitable for use in the present invention as long as they can be moved from an open configuration to a closed and locked configuration such that they do not spontaneously reopen. In the open configuration, a suitable clip can receive a catheter without a need to thread the catheter through the clip. In the closed and locked configuration, the clip allows the catheter to move in both axial directions and to rotate within the clip, but constrains the lateral and vertical movement of the catheter.

Continuing to refer to FIGS. 3 and 4, the exemplary clip 22 has a body 26 that includes a curved rod 28 with a lyre-like shape. In an embodiment, the body 26 is formed from a resilient material so that it may be moved from an open configuration (FIG. 3) to a closed configuration (FIG. 4), then moved back to the open configuration. The body 26 has a generally U-shaped base 30 and a pair of movable members 32, 34 that may be moved to change the configuration of the clip 22. In the present embodiment, the moveable members include a first arm 32 and a second arm 34 opposite the first arm 32. Both arms are curved so that they can be interlocked (see FIG. 4) by twisting them around each other. At the end of each arm 32, 34 are balls 36, 38, which are integral to the respective arms 32, 34, and formed to hold the arms 32, 34 in place by obstruction when the arms 32, 34 are interlocked.

Figure 5:
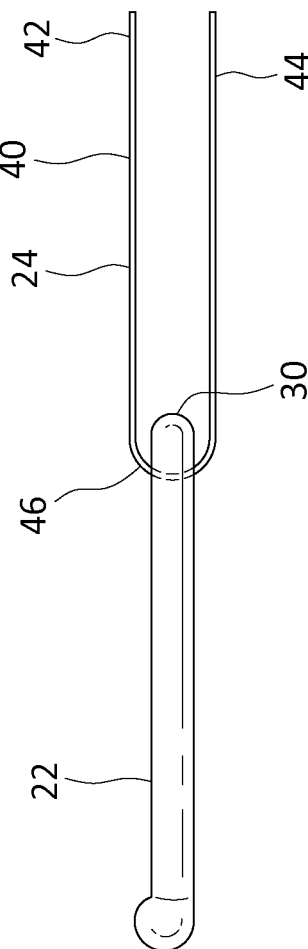
FIG. 5 is a side elevation view of the clip and fabric strip of FIG. 3 according to an embodiment of the present invention.
Figure 6:
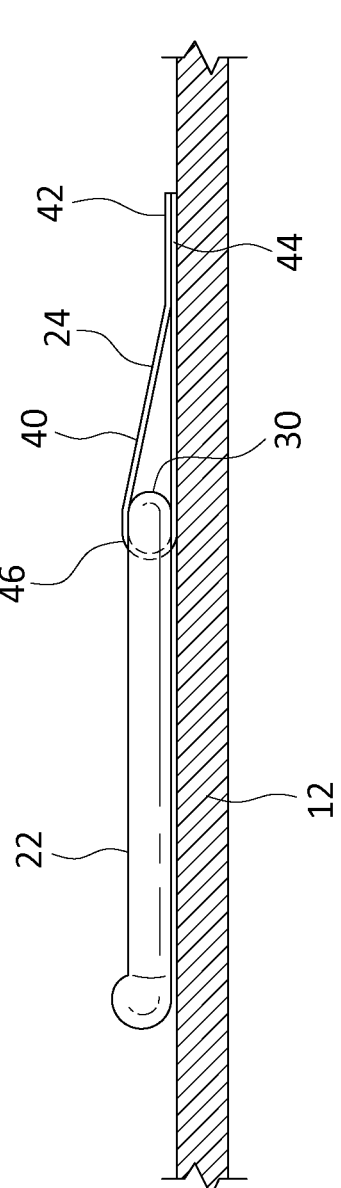
FIG. 6 is a front elevation view of the clip and fabric strip of FIG. 5 with the fabric strip arranged as a loop attached to a drape.

Turning to FIGS. 5 and 6, the tethering means 24 of the exemplary embodiment includes a strip of fabric 40 having a first end 42 and a second end 44 opposite the first end 42. The fabric strip 40 forms a loop 46 around the base 30 of the clip 22, and the ends 42, 44, are attached to the drape 12. In the embodiment of FIG. 6, the ends 42, 44 of the fabric strip 40 are attached to each other and to the drape 12 at the same location on the drape 12. In other embodiments which are not shown in the figures, the ends 42, 44 of the fabric strip 40 are attached to the drape 12 at different locations on the drape 12, or the fabric strip 40 forms a loop 46 around the base 30 with one end 42 of the fabric strip 40 attached to the fabric strip 40, and the other end 44 attached to the drape 12. In another embodiment (not shown), the fabric strip 40 lays flat on the drape 12 with the ends 42 and 44 attached to the drape 12 such that the base 30 of the clip 22 is retained between the fabric strip 40 and the drape 12. In embodiments of the invention, tethering means other than fabric strips may be used. Suitable tethering means include, but are not limited to plastic, foil, or metal strips, yarns, threads, filaments, meshes, and similar items that can tether a clip to a drape while allowing the clip to be moved relative to the drape. Turning to FIGS. 7 and 8, the clip 22 and fabric strip 40 are movable relative to each other and to the drape 12 to the limits at which they are obstructed from moving further. For example, the clip 22 may rotate within the loop 46 from a first position P1 where it is substantially flat against the drape 12, continuously through a position P2 that is at an angle of 90° relative to the drape 12, then continuously to a position P3 where it is substantially flat against the fabric strip 40. The loop 46 of fabric strip 40 can be lifted from a position P4 where it is substantially flat against the drape 12, continuously through a position P5 that is an angle of 90° relative to the drape 12, then continuously to a position P6 where its further movement is obstructed by its ends 42, 44.

In an embodiment of a method of using a catheter organizer of the present invention, the drape is draped over a patient, and a catheter is inserted into a vein or artery at a vascular access point. The clips along a desired pathway for routing are then opened. In an exemplary embodiment, the pathway is at least partially defined by a longitudinal linear array of clips. The catheter, with or without additional elongated elements, is then positioned in the openings of the clips, and the clips are closed. Thus, the catheter and/or other elongated elements, are restrained from moving laterally relative to the body 26 of the clip 22, while rotation, withdrawal, and advancement of the catheter and/or other elongated elements within the clips is permitted, thereby preventing entanglement of catheters and tubing and the adverse consequences thereof. In embodiments having clips that may be reversibly closed and opened, such as clip 22, the clips may be opened during the procedure to allow catheters, elongated elements, or implements to be added, removed, or repositioned. After the procedure has been completed, the clips can be opened so that the catheters, elongated elements, or implements may be removed before the patient is moved or uncovered. In some situations, it may be desirable to remove the catheters and elongated elements by pulling them in a longitudinal direction through the closed clips.

Figures 10, 11:
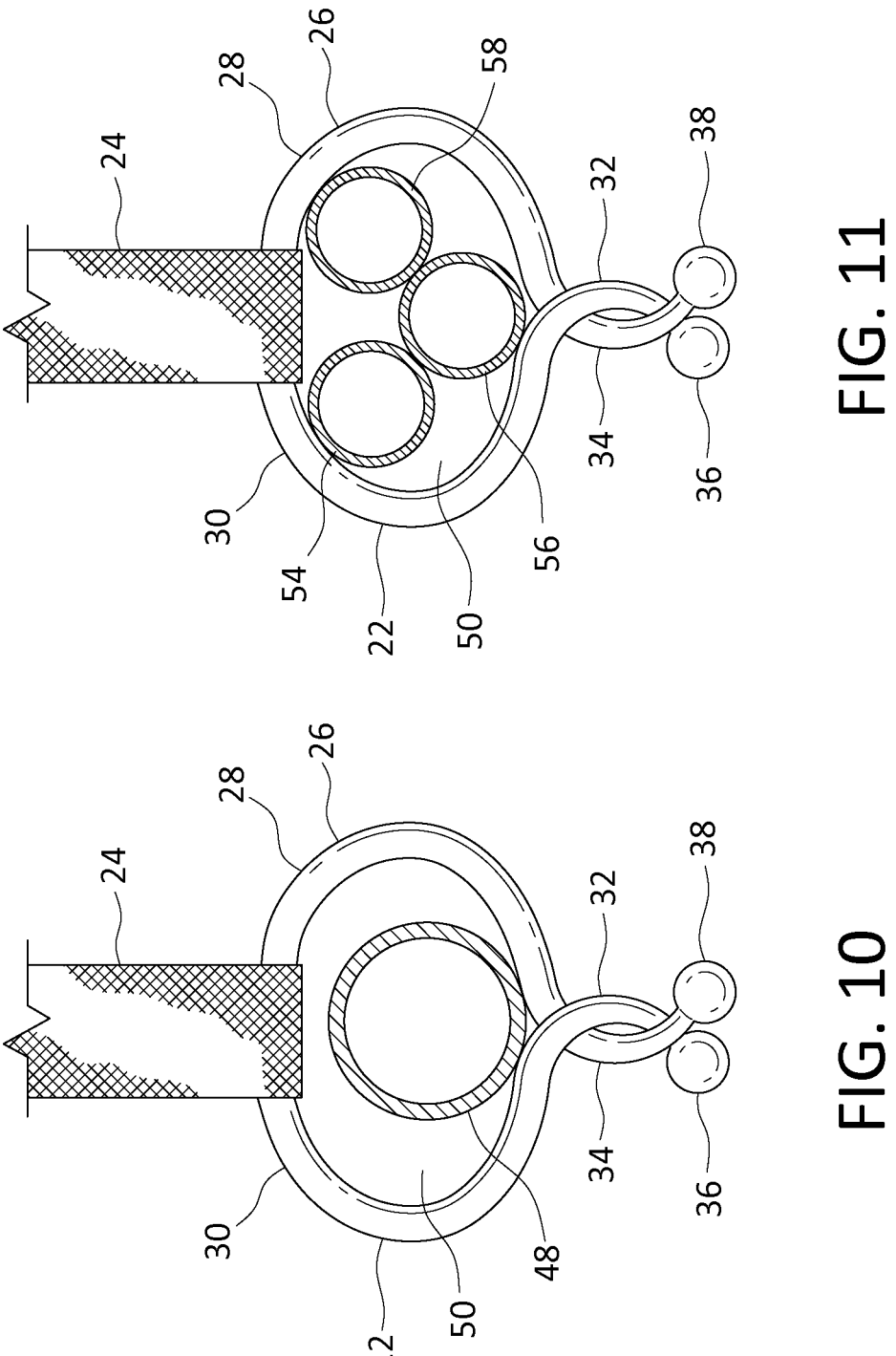
FIG. 10 is a front elevation view of the clip and fabric strip of FIG. 9, with the clip in a closed configuration and the tube within the clip, according to an embodiment of the present invention.
FIG. 11 is a front elevation view of a clip and fabric strip arranged as in FIG. 10, having a plurality of tubes retained by the clip, the plurality of tubes shown in an axial cross-sectional view.

FIG. 9 is an illustration of a typical clip 22 in its open configuration with a catheter 48 (seen in cross-section) being moved into the interior 50 of the clip 22 through a space 52 between the arms 32, 34. With the catheter 48 within the interior 50 of the clip 22, the arms 32, 34 are twisted about each other, closing the clip 22 and causing the arms 32, 34 to intertwine (FIG. 10). The intertwined arms 32, 34, in conjunction with the balls 36, 38, lock the clip 22 in its closed configuration, thereby restraining the catheter 48 from moving laterally relative to the body 26 of the clip 22, while allowing the catheter 48 to move longitudinally or rotate within the clip 22.

Clips, such as clip 22, may be selected according to the size of the catheter, other elongated element, or implement that is to be retained. In an embodiment of the method of the present invention, the clip 22 may be selected to retain more than one catheter, such as catheters 54, 56, 58 of FIG. 11.

Figure 12:
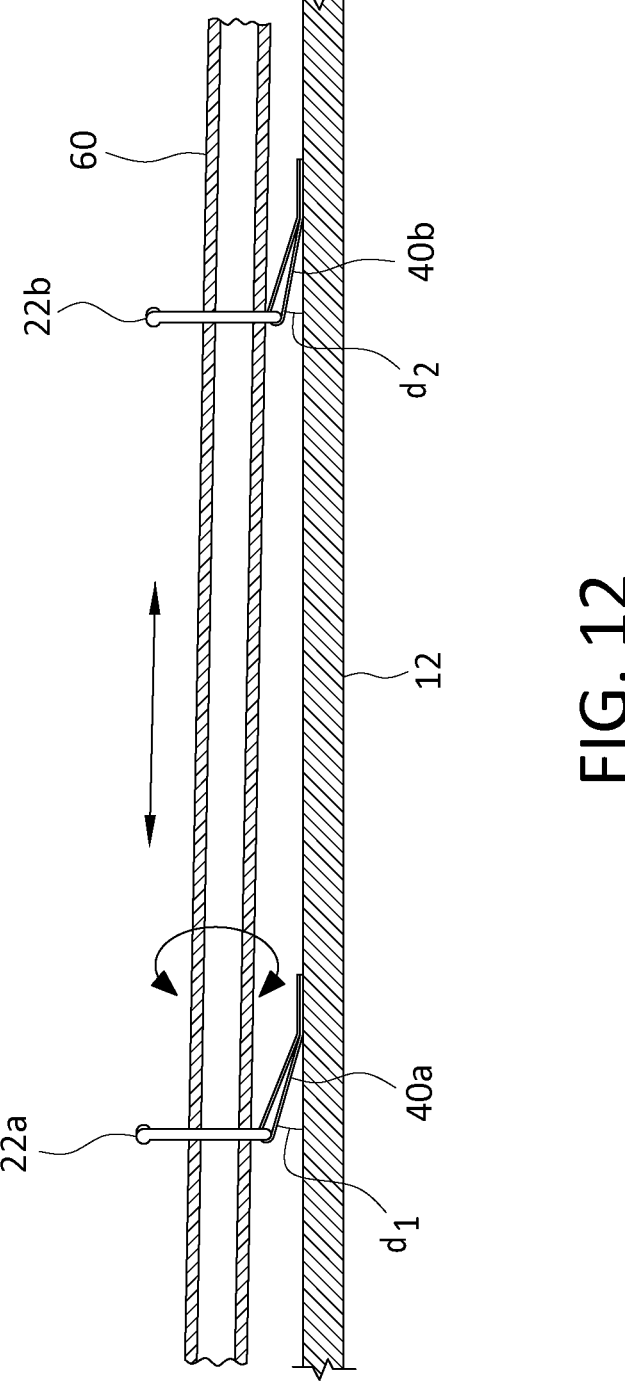
FIG. 12 is a side elevation view of two clips retained by fabric loops as in FIG. 6 and a tube passing through the clips according to an embodiment of the present invention.

FIG. 12 is an illustration of a catheter 60 retained by representative clips 22a and 22b, which, respectively, are tethered to the drape 12 by fabric strips 40a, 40b. Clips 22a, 22b move independently of each other as the catheter 60 moves during a procedure. Movement of catheter 60, may thus cause clips 22a, clip 22b to be moved vertically to different distances from the drape 12 (e.g., d1>d2), or in different lateral or longitudinal directions within the range of movement allowed by the fabric strips 22a, 22b.

The foregoing Detailed Description is to be understood as being in every respect illustrative and exemplary, but not restrictive, and the scope of the invention disclosed herein is not to be determined from the Detailed Description, but rather from the appended claims as interpreted according to the full breadth permitted by the patent laws. Accordingly, various modifications, including other arrangements of features, may be implemented by those skilled in the art without departing from the scope of the invention.

I claim:

1. A catheter organizer for organizing one or more catheters during a surgical procedure, comprising
a drape; and
a plurality of retaining means attached to said drape, each of said plurality of retaining means having a clip and a tether that tethers said clip to said drape and said tether is not attached to said clip, wherein said clip is arranged to removably receive the one or more catheters such that the one or more catheters move longitudinally and rotate within said clip, said clip having movable members for changing said clip from an open configuration to a closed configuration by manipulation of said movable members, at least some of said plurality of retaining means aligned with others of said plurality of retaining means so that said aligned plurality of retaining means receive and retain the one or more catheters.

2. The catheter organizer of claim 1, wherein said plurality of retaining means are arranged to provide one or more pathways for routing the one or more catheters along or across said drape.

3. The catheter organizer of claim 1, wherein said tether has a first end and a second end opposite the first end, the first end attached to said drape and said second end retaining said clip so that said clip moves from a first position to a second position relative to said drape without separating from said tether.

4. The catheter organizer of claim 1 in combination with the one or more catheters received and retained in at least one of said clips.

5. The apparatus of claim 1, wherein said tether has a first end and a second end opposite said first end, said first end attached to a first location on said drape and said second end attached to a second location on said drape, said clip is restrained by said tether between said first end and said second end, and said clip is moveable along said tether between said first end and said second end.

\* \* \* \* \*